United States Patent [19]

Wang

[11] Patent Number: 5,137,633

[45] Date of Patent: Aug. 11, 1992

[54] HYDROPHOBIC MEMBRANE HAVING HYDROPHILIC AND CHARGED SURFACE AND PROCESS

[75] Inventor: David Wang, Lexington, Mass.

[73] Assignee: Millipore Corporation, Bedford, Mass.

[21] Appl. No.: 721,737

[22] Filed: Jun. 26, 1991

[51] Int. Cl.⁵ .............................................. B01D 67/00
[52] U.S. Cl. .................. 210/490; 210/500.35
[58] Field of Search .................. 210/490, 500.35, 638; 427/245; 264/41, 22

[56] References Cited

U.S. PATENT DOCUMENTS 4,908,236  3/1990  Pitt et al. .................. 210/500.35 X Primary Examiner—Frank Spear
Attorney, Agent, or Firm—Paul J. Cook; Andrew T. Karnakis

[57] ABSTRACT

The surface of a hydrophobic porous substrate is modified with an interpolymeric network of a hydrophilic crosslinked polymer and a crosslinked-polyamine epichlorohydrin resin having fixed positive charges. The hydrophobic substrate is contacted with a reaction system comprising a solution of (a) monomer precursor to the hydrophilic polymer, a nonionic or cationic polymerization initiator and a crosslinking agent and (b) a precursor to the crosslinked positively charged resin. The monomer is polymerized and cross-linked by free radical polymerization followed by heating the contacted substrate to form the charged resin.

16 Claims, No Drawings

HYDROPHOBIC MEMBRANE HAVING HYDROPHILIC AND CHARGED SURFACE AND PROCESS

BACKGROUND OF THE INVENTION

This invention relates to hydrophobic porous surfaces a charge-modified, hydrophilic surface and to a method for making the same. More particularly, this invention relates to such surfaces and to a one-step process for modifying a hydrophobic surface to render it hydrophilic and positively charged.

Porous surfaces in the form of a membrane or a nonwoven fabric are utilized extensively in separations technology. Microporous membranes have been demonstrated to have utility in a wide variety of applications. As such, numerous processes have been developed to produce such membranes. For example, U.S. Pat. No. 3,876,783 describes a process for preparing a microporous membrane by quenching a solution of a film forming polymer in a non-solvent system for the polymer. European Patent Application No. 0 005 536 describes a similar process.

Commercially available microporous membranes, comprising for example, nylon, are available from Pall Corporation, Glen Cove, N.Y. under the trademark ULTIPOR $N_{66}$. Additionally, microporous membranes made of cellulose acetate, cellulose nitrate or mixtures thereof are widely available from a variety of sources. Other membranes, comprising polyvinylidene fluoride (PVDF), are available under the trademark Durapore ® (Millipore Corporation, Bedford, Mass.). The nylon and nitrocellulose membranes exhibit hydrophilic properties, while the PVDF membranes are hydrophobic. It is possible, however, to coat the PVDF membranes with materials which render them hydrophilic. These hydrophilic Durapore ® membranes are also available from the Millipore Corporation.

For certain applications, notably filtration and macromolecular transfer, it has been suggested that the performance of the material could be increased by providing an ionic functional group attached to the membranes which would serve to provide a fixed formal positive charge to the membranes. Such charge-modified membranes have been suggested for macromolecular transfer applications (e.g., DNA and protein blotting) in U.S. Pat. Nos. 4,512,896 and 4,673,504. Additionally, charge modified membranes have been suggested for use as filtration materials in U.S. Pat. Nos. 4,473,474 and 4,673,504. In each of these, however, the invention is limited to methods for charge-modifying hydrophilic membranes and the use of the same. The latter two patents each provide an example describing unsuccessful attempts to charge-modify hydrophobic membranes.

As such, the charge-modified microporous membranes used for macromolecular blotting and filtration applications have utilized hydrophilic membranes as starting materials.

The term "macromolecular blotting" as used herein refers to processes for transferring biological macromolecules such as nucleic acids and proteins from electrophoresis gels to some type of immobilizing matrix. Of particular importance is nucleic acid blotting such as DNA blotting. A variety of DNA blotting techniques have been developed. The most common technique is referred to as "Southern blotting". In this technique, DNA fragments are separated by chromatography and then denatured while still in the gel. The gel is neutralized and placed between wicking paper which is in contact with a buffer reservoir. Nitrocellulose is then placed on top of the gel and dry blotting papers are placed on top of the nitrocellulose. As the buffer flows into the gel, DNA is eluted and binds to the nitrocellulose, thereby transferring the DNA fragment pattern onto the nitrocellulose. The fragment pattern can then be detected using hybridization techniques employing labelled nucleic acids which are complementary to the specific bound fragments.

Since the original development of the Southern blotting technique, a number of variations and improvements have been developed. For example, if the blotting paper is derivatized with diazobenzyloxymethyl groups, thereby forming a material commonly referred to as DBM-paper, RNA and proteins can be covalently attached to the material. Other immobilization methods have used high salt or alkaline conditions, i.e, efforts to improve binding of DNA, RNA and proteins.

Other attempts to improve the binding process have concentrated on the blotting substrate by replacing nitrocellulose, for example, with other hydrophilic materials such as Nylon 66. Additionally, U.S. Pat. Nos. 4,512,986 and 4,673,504, previously described, suggest other materials such as hydrophilic charged PVDF for use as blotting substrates.

U.S. Pat. No. 4,618,533 discloses a process for rendering the surface of a porous hydrophobic membrane hydrophilic while avoiding substantial blockage of the pores. While a charged hydrophilic surface is disclosed, the product has a very low ion exchange capacity of about 0.005 meq/g.

SUMMARY OF THE INVENTION

This invention provides porous surfaces in the form of a nonwoven fabric or a membrane formed from a hydrophobic polymer material and having surfaces which are modified to render them hydrophilic and charged with positively charged groups. The surface is rendered hydrophilic with a cross-linked polymer formed from a monomer polymerized in situ with a nonionic or cationic polymerization initiator and cross-linked in situ on the hydrophobic porous substrate. The fixed positive charge groups result largely from quaternary or tertiary ammonium functional groups which are provided on the porous surface by contacting the porous surface with a solution containing a polyamine or polyamide-polyamine epichlorohydrin cationic resin to provide a surface coating. As used herein, the term "polyamine-resin" or "polyamine-epechlorohydrin resin" includes polyamine resins or polyamine-polyamide resins. The precursor monomers to the hydrophilic polymer and to the epichlorohydrin compound are applied to the hydrophobic membrane substrate in a single contacting step. The contacted porous substrate then is exposed to an energy source such as ultraviolet light to initiate free radical polymerization of the monomer followed by heating of the membrane to cross link the polyamine resin. The resultant modified surface is both hydrophilic and charge-modified with positive charges and comprises an interpenetrating polymeric network formed from the hydrophilic polymer and the polymer having the positive charges. The membranes of this invention are particularly well suited for macromolecular blotting or filtration application.

DESCRIPTION OF SPECIFIC EMBODIMENTS

The modified porous substrates comprise hydrophobic, microporous or ultrafiltration membranes or nonwovens the surfaces of which have been rendered hydrophilic with a cross-linked hydrophilic polymer and charge-modified with a polymer having fixed charge groups having a net positive charge. The charge modified polymer and the hydrophilic polymer form an interpenetrating polymeric network rather than a layered coating formed from the two polymers so that the exposed surface is both hydrophilic and charge modified.

The term "microporous membrane" as used herein defines a porous membrane having an average pore size of between about 0.05 and 10 microns or an initial bubble point (IBP) in water of less than 120 psi. Ultrafiltration membranes can also be modified in accordance with this invention and comprise anisotropic or asymetrical membranes are also available formed as a composite between a thin layer of a material having a small average pore size supported by a more porous structure.

Hydrophobic membranes or nonwovens useful for this invention include those comprising hydrophobic or nonwoven polyolefins such as polymethylpentene, polypropylene, polyethylene, polysulfone, polyethesulfones,polyimides, polyetherimides, polytetrafluoroethylene (PTFE), polyvinylidene fluoride (PVDF), polyesters including polyethylene terephthalate, polybutylene terephthalate, polycarbonate, vinyl polymers such as polyvinyl chloride and polyacrylonitriles. Copolymers also can be employed such as copolymers of butadiene and styrene, brominated ethylene-propylene copolymer, ethylene-chlorotrifluoroethylene copolymer or the like. PVDF membranes are preferred and are known in the art, being described, for example in U.S. Pat. Nos. 4,203,848 and 4,203,847, the teachings of which are incorporated herein by reference. Furthermore, these hydrophobic membranes are commercially available as, for example, Immobilon P ® microporous membranes (Trademark of Millipore Corporation, Bedford, Mass.).

The surfaces of the hydrophobic substrate are modified by passing the substrate through a solution comprising (a) a hydrophilizing component of a monomer capable of being polymerized by free radical polymerization and which is cross-linked an optional crosslinking agent and a nonionic or cationic polymerization initiator for the monomer and (b) a charge-modifying agent comprising a polyamine epichlorohydrin cationic resin. Anionic polymerization initiators can not be used since they promote undesirable precipitation of the cationic resin. The substrate then is exposed to an energy source for initiating free radical polymerization such as ultraviolet light in order to polymerize and cross-link the precursor to the hydrophilic polymer. In addition, some crosslinking of the polyamine resin occurs in this step. The membrane is exposed to heat in order to more completely cross-link the polyamine-polyamide epichlorohydrin resin. The resultant product comprises a hydrophobic porous substrate having its surfaces coated with an interpenetrating polymeric network formed of the crosslinked hydrophilic resin and the crosslinked polyamine epichlorohydrin resin. As a result, the membrane has a surface which is hydrophilic and has fixed positive charges.

The polymerization and cross-linking of the polymerizable monomer to the porous substrate by grafting and/or deposition is effected so that the entire surface of the porous substrate including the inner surfaces of the pores is coated with a cross-linked polymer which forms part of the interpolymeric network. In a first step, the porous substrate can be washed with a solvent composition that does not substantially swell or dissolve the porous membrane and which wets the surfaces of the pores such as a mixture of water and an organic solvent. Suitable water-solvent or organic solvent compositions for this purpose include methanol/water, ethanol/water, isopropanol/water, acetone/water, tetrahydrofuran/water or these organic solvents alone or the like. The purpose of this wetting step is to assure that the monomer composition subsequently contacted with the porous substrate wets the entire surface of the porous substrate. This preliminary wetting step can be eliminated when the reagent bath described below itself functions to wet the entire surface of the porous substrate. This can be effected when the reagent both contains a high concentration of organic reactants, for example 15% by weight or higher. In any event, all that is required is that the entire porous surface be wet so that the polymerizable monomer wets the entire surface of the porous substrate.

Subsequent to wetting the porous substrate, a reagent bath comprising the hydrophilic polymer precursor, i.e. a free radical polymerizable monomer, a nonionic or cationic polymerization initiator and a cross-linking agent together with the precursor constituents of the polyamine epichlorohydrin resin in a solvent for these four constituents are contacted with the porous hydrophobic substrate under conditions to coat the substrate with these precursor constituents. When the monomer for the hydrophilic polymer is difunctional or has higher functionality it can function as a crosslinking agent and, an additional cross-linking agent need not be utilized.

Any monomer for forming the hydrophilic polymer can be utilized herein so long as it is capable of being polymerized by free radical polymerization and it can be cross-linked. Representative suitable polymerizable monomers include hydroxyalkyl acrylates or methacrylates, including hydroxyalkyl acrylates or methacrylates, including 1-hydroxyprop-2-yl acrylate and 2-hydroxyprop-1-yl acrylate, hydroxypropyl methacrylate, 2,3-dihydroxypropyl acrylate, hydroxyethyl acrylate, hydroxyethyl methacrylate or the like or mixtures thereof. Other polymerizable monomers which can be utilized herein include acrylic acid, acrylamides, methacrylamides, ethacrylamides, etc. These monomers are examples of polar-substituted or functionally substituted monomers useful herein.

Suitable nonionic or cationic initiators and cross-linking agents for the monomers set forth above are well known in the art. The nonionic or cationic initiators can be photoinitiators, thermal initiators or both. Examples of photoinitiators include benzophenone, benzoin methyl ether, 4-(2-hydroxyethoxy) phenyl-(2-hydroxy-2-propyl) ketone or the like. Suitable thermal initiators include azobis isobutyramodine hydrochloride (available under the tradename, Darocur 2979), hydrogen peroxide, benzoyl peroxide or the like. When utilizing acrylates or methacrylates or methacrylamides as the polymerizable monomer, suitable cross-linking agents include difunctional acrylates, methacrylates or acrylamides such as tetraethylene glycol diacrylate or methylene bisacrylamide or the like. In one embodiment of this invention, cross-linking agents having difunctionality or higher functionality can be utilized without an additional cross linker in the coating of this invention. The monomer, nonionic or cationic polymerization initiator and optional cross-linking agent as well as the polyamine epichlorohydrin resin are contacted with the porous substrate as a mixture in a solvent. The solvent is compatible with the these reactants and the porous substrate so that the desired free radical polymerization and cross-linking is achieved.

The particular solvent employed for the polymerizable monomer, polymerization initiator and cross-linking agent will depend upon the particular reactants employed and upon the particular polymer utilized to form the porous substrate. All that is necessary is that the reactants dissolve in the solvent and are capable of being reacted by free radical initiation in the solvent system and the solvent does not attack the porous substrate. Thus the particular solvent system used will depend upon the reactants and porous substrates employed. Representative suitable solvents include water or organic solvents such as alcohols, esters, acetone or compatible aqueous mixtures thereof.

Generally, the polymerizable monomer is present in the reactant solution at a concentration between about 1% and about 20%, preferably between about 3% and about 9% based upon the weight of the reactant solution. The cross-linking agent generally is present in an amount of between about 0.01% and about 90% by weight, preferably between about 0.1% and about 1% by weight based upon the weight of the polymerizable monomer. Greater amounts of cross-linking agents can be used but no significant advantage is gained thereby. The nonionic or cationic polymerization initiator is present in an amount of between about 0.1% and about 10% by weight, preferably between about 1% and about 5% by weight, based upon the weight of the polymerizable monomer.

Any conventional energy source for initiating free radical polymerization can be employed such as heating, ultraviolet light, gamma radiation, electron beam radiation or the like. For example, when free radical polymerization is initiated by heating, the reactant solution and the porous substrate are heated to a temperature at least about 60° C. and up to the temperature at which undesirable bulk polymerization occurs in solution or at which the solvent begins to boil. For example, generally suitable temperatures when utilizing an aqueous solvent system between about 80° C. and about 95° C., preferably between about 88° C. and about 92° C. The polymerization reaction should be effected for a time to assure that the entire exposed surface of the porous substrate is coated with the deposited cationic hydrophilic interpolymer composition but without significant plugging of the pores in the porous substrate. Generally, suitable reaction times are between about 0.1 and about 30 minutes, preferably between about 0.1 and about 2 minutes.

The charge-modifying agent used in this invention to form a portion of the interpolymeric network coating for this porous substrate is a water soluble organic polymer having a molecular weight greater than about 1000, wherein the polymer comprises monomers units, the majority of which have been reacted with epichlorohydrin. The epichlorohydrin serves to convert some of the tertiary amine structures on the polymer to structures having a quaternary functionality, which can be further reacted to produce crosslinking. This provides a stable coating which comprises a quaternary ammonium fixed formal charge capable of conferring a net positive charge to the hydrophobic substrate.

The charge-modifying agent is coated onto the contacted surfaces of the hydrophobic microporous substrate as described above. The term "coated" as used herein refers to charge-modifying agents which are sufficiently attached to the substrate so that they will not significantly extract under the intended conditions of use.

The charge-modifying resins are preferably polyamine epichlorohydrin cationic resins, such as those described in U.S Pat. Nos. 2,926,116; 3,224,986; 3,311,594; 3,332,901; 3,382,096; and 3,761,350, of which the teachings of each are incorporated herein by reference. The process of this invention also can be utilized with a secondary charge modifying agent as disclosed in these patents.

It is required that the charge-modifying agent contain halohydrin substituents as well as fixed formal positive charge groups. Agents containing epichlorohydrin substitutents and quaternary ammonium ions are most preferred. One such charge-modifying agent is the polyamine epichlorohydrin resin available commercially as R4308 resin (Trademark of Hercules Corp., Wilmington, Del.). In this resin, the charged nitrogen atom forms part of a heterocyclic grouping, and is bonded through a methylene moiety to a pendent chlorohydrin group. Each monomer group of Hercules R4308 is represented by the following general formula:

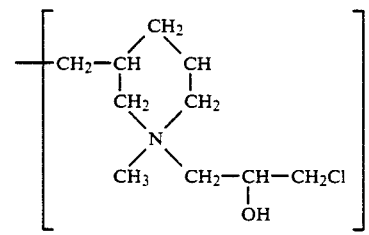

Another preferred charge modifying agent is Polycup 1884 (Trademark of Hercules Corp , Wilmington, Del.), the individual monomers of which are represented by the following general formula:

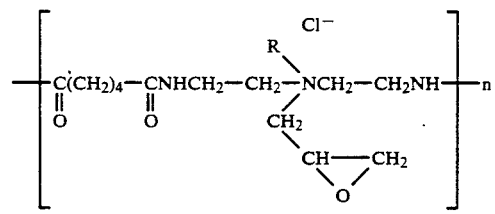

It is be pointed out, however, that ions other than ammonium ions, such as sulfonium, phosphonium or the like which form fixed formal positive charge groups can be used in the practice of this invention as well. The charge-modifying agent is preferably a polyamine epichlorohydrin resin and is present in the solution of the water-miscible organic solvent as between about 0.5% and 15% solids by weight, however, a solution of between about 1% and 3% solids by weight is preferred. The organic solvent can be any of the lower alcohols routinely used in industrial processing. Methanol, ethanol, isopropanol and mixtures thereof are preferred.

This alcohol/water mixture is typically a 10–50% mixture by weight depending upon the solvent. The mixture is rendered mildly alkaline by the addition of a material such as NaOH. Preferably the solution is at a pH of between about 9.0 and 12.0.

The following examples illustrate the present invention and are not intended to limit the same.

EXAMPLE I

This example illustrates rendering the surface of a hydrophobic porous substrate formed from PVDF hydrophilic and positively charged. The untreated substrate were formed of 47 mm discs having an average pore size of 0.22 um.

A plurality of reactive baths shown in Table I were formed from (a) a mixture of 2-hydroxyprop-1-yl acrylate (75%) and 1-hydroxyprop-2-yl acrylate (25%) (HPA), (b) R 4308 cationic resin reaction mixture, (c) tetraethylene glycol diacrylate (TEGDA) and (d) nonionic polymerization initiator Darocur 2959. In each instance, the substrate was saturated with the reaction mixture, exposed to ultraviolet light at 200–400 nanometer for 20 seconds followed by heating at between 170° and 176° F. for 1–2 minutes membranes were rinsed in deconized water for 2 minutes and dried. Wetting time of the treated substrate was determined by the following procedure. A drop of deionized water is placed on the surface of the membrane and the time of wicking of the drop into the membrane is timed in seconds. If less than one second, the wetting time is considered to be instantaneous. If after one minute there is no evidence of any wicking, the membrane is considered phobic. Ion exchange capacity of the treated substrate was determined by the following procedure: 47 mm discs of membrane samples are placed in 100 ml. of 0.1M HCl in 50% (V/V) methanol for 5 minutes followed by air drying. The membrane disks are then wet in 100 ml. of 80% (V/V) methanol/water mixture to which 2 ml. of 5M NaNO$_3$ solution is added. The chloride ion concentration is then estimated by derivative titration with silver nitrate (0.0282M AgNO$_3$) using a Fisher computer aided titrimeter. The IEC capacity is then expressed as microequivalents per disc.

TABLE I

| | Formulation (wt %) | | | | |
|---|---|---|---|---|---|
| R 4308 | HPA | TEGDA | Darocur 2959 | Wet Time | IEC |
| 0.5 | 3.75 | .375 | .1875 | 1 | 3.10 |
| 1.0 | 2.5 | .25 | .125 | 20 sec | 2.25 |
| 1.5 | 1.25 | .125 | .0625 | phobic | 2.82 |

Note: I = Instantaneous

As shown in Table I, the wetting time was dependent on the concentration of HPA. The IEC reflects the presence of cationic charge, although the IEC levels were not correlated to R-4308 levels.

EXAMPLE II

The procedure of Example I was repeated except that the substrate disc was pretreated in isopropyl alcohol to prewet the substrate and exposure to UV was as above. The UV treated disc was rinsed in water for 2 minutes and the disc was dried at room temperature.

The coating formulation and product characteristics are shown in Table II.

TABLE II

| R 4308 | HPA | TEGDA | Darocur 2959 | Wet Time | IEC |
|---|---|---|---|---|---|
| 3.0 | 3.45 | .345 | .173 | <2 sec | 12.97 |

This shows that by increasing the R-4038 amount, and maintaining the HPA at the level for good wetting time from Table I, a philic membrane with high IEC can be attained.

EXAMPLE III

The procedure of Example II was repeated except the water rinse step was eliminated and drying and baking was effected at 50° C. The membranes then were rinsed in deionized water for 2 minutes and dried. The results are shown in Table III.

TABLE III

| Wet Time | IEC |
|---|---|
| I | 27 |

The IEC can be increased further by not rinsing the membrane immediately after the UV process. The philic character of the membrane was not affected.

I claim:

1. A porous hydrophobic filter substrate having its surface modified with a coating to render the surface hydrophilic and modified with positive charges, said coating comprising an interpenetrating polymeric network comprising:
   (a) a first polymeric composition of a polyamide polyamine epichlorohydrin cationic charge modifying agent having tertiary amine or quaternary ammonium groups crosslinked in situ on said surface and
   (b) a crosslinked polymer formed from a monomer polymerized in situ on said surface with a nonionic or cationic free radical initiator and crosslinked in situ on said substrate,
   said composite porous substrate having essentially the same porous configuration as said hydrophobic porous filter substrate.

2. The modified filter substrate of claim 1 wherein said substrate is a porous membrane.

3. The modified filter substrate of claim 2 having an average pore size between about 0.05 and 10 microns.

4. The modified filter substrate of claim 1 wherein said substrate is a porous nonwoven substrate.

5. The modified hydrophobic filter substrate of claim 1 wherein said crosslinked second polymer is derived from an acrylate.

6. The modified hydrophobic filter substrate of any one of claims 1, 2, 3 or 4 wherein said hydrophobic substrate is a fluorinated ethylene polymer.

7. The modified hydrophobic filter substrate of any one of claims 1, 2, 3 or 4 wherein said hydrophobic substrate is polyvinylidene fluoride.

8. The modified hydrophobic filter substrate of any one of claims 1, 2, 3 or 4 wherein said hydrophobic substrate is a polyolefin.

9. The modified hydrophobic filter substrate of any one of claims 1, 2, 3 or 4 wherein said hydrophobic substrate is a polyester.

10. The modified hydrophobic filter substrate of any one of claims 1, 2, 3 or 4 wherein said hydrophobic substrate is a polysulfone.

11. The modified hydrophobic filter substrate of any one of claims 1, 2, 3 or 4 wherein said hydrophobic substrate is a polyetherimide.

12. The modified hydrophobic filter substrate of any one of claims 1, 2, 3 or 4 wherein said hydrophobic substrate is a polyethylene sulfone.

13. The process for forming the surface modified substrate of claim 1 which comprises;
 (A) contacting a hydrophobic porous substrate with a solution of
  (a) a polymerizable hydrophilic monomer, a cross-linking agent for said hydrophilic monomer and a nonionic or cationic polymerization initiator for said monomer and
  (b) a long chain polyamine-epichlorohydrin reaction product,
 (B) polymerizing and cross-linking said monomer by free radical polymerization in situ on said substrate and
 (C) cross linking said polyamine epichlorohydrin charge modifying agent to produce a crosslinked polymer having tertiary amine and quaternary ammonium groups in situ on said substrate.

14. The process of claim 13 wherein said hydrophilic monomer also comprises said cross-linking agent.

15. The process of any one of claim 13 or 14 wherein said substrate is a membrane.

16. The process of any one of claims 13 or 14 wherein said substrate is a porous nonwoven substrate.

* * * * *